United States Patent
Xu et al.

(10) Patent No.: US 11,389,592 B2
(45) Date of Patent: Jul. 19, 2022

(54) VENTING COMPONENT, CATHETER AND SYRINGE INCLUDING THE SAME

(71) Applicants: HEFEI BOE OPTOELECTRONICS TECHNOLOGY CO., LTD., Anhui (CN); BOE TECHNOLOGY GROUP CO., LTD., Beijing (CN)

(72) Inventors: Fei Xu, Beijing (CN); Lei Lv, Beijing (CN); Jun Hong, Beijing (CN); Chunmin Xu, Beijing (CN); Jie Gao, Beijing (CN)

(73) Assignees: HEFEI BOE OPTOELECTRONICS TECHNOLOGY CO., LTD., Anhui (CN); BOE TECHNOLOGY GROUP CO., LTD., Beijing (CN)

( * ) Notice: Subject to any disclaimer, the term of this patent is extended or adjusted under 35 U.S.C. 154(b) by 387 days.

(21) Appl. No.: 16/500,205

(22) PCT Filed: Mar. 29, 2019

(86) PCT No.: PCT/CN2019/080277
§ 371 (c)(1),
(2) Date: Oct. 2, 2019

(87) PCT Pub. No.: WO2019/205884
PCT Pub. Date: Oct. 31, 2019

(65) Prior Publication Data
US 2021/0402098 A1    Dec. 30, 2021

(30) Foreign Application Priority Data
Apr. 28, 2018   (CN) .......................... 201810404062.7

(51) Int. Cl.
*A61M 1/00*   (2006.01)
*A61M 5/31*   (2006.01)
(Continued)

(52) U.S. Cl.
CPC ................ *A61M 5/31* (2013.01); *A61M 5/40* (2013.01); *A61M 25/0097* (2013.01); *A61M 2005/3123* (2013.01)

(58) Field of Classification Search
CPC ........ A61M 5/31; A61M 5/40; A61M 5/1685; A61M 5/36; A61M 5/3123; A61M 5/14; A61B 5/150213
See application file for complete search history.

(56) References Cited

U.S. PATENT DOCUMENTS

2002/0165490 A1* 11/2002 Minezaki .......... A61M 5/14526
604/151
2004/0092905 A1   5/2004 Azzolini
(Continued)

FOREIGN PATENT DOCUMENTS

CN   203862007 U    10/2014
WO   2017/091643 A1   6/2017

OTHER PUBLICATIONS

First Office Action and English language translation, CN Application No. 201810404062.7, dated Oct. 11, 2019, 10 pp.

*Primary Examiner* — Rebecca E Eisenberg
(74) *Attorney, Agent, or Firm* — Myers Bigel, P.A.

(57) ABSTRACT

A venting component includes a chamber, a vent hole and a floating block. The chamber includes a bottom chamber and an extended chamber communicating with the bottom chamber and extending upward therefrom. The bottom chamber is configured for liquid to flow in and out. The extended chamber includes a support portion. The vent hole is located at a side of the extended chamber away from the bottom chamber. The floating block is located in the extended chamber and forms a gap with the chamber wall of the (Continued)

extended chamber. The floating block is configured to be supported on the support portion and dimensioned to be able to block the vent hole.

13 Claims, 3 Drawing Sheets

(51) Int. Cl.
*A61M 5/40* (2006.01)
*A61M 25/00* (2006.01)

(56) References Cited

U.S. PATENT DOCUMENTS

| | | | |
|---|---|---|---|
| 2005/0283123 A1* | 12/2005 | Lyde | A61M 5/40 604/254 |
| 2010/0225494 A1* | 9/2010 | Thorpe | A61M 5/1411 340/632 |
| 2018/0344571 A1 | 12/2018 | Cowan et al. | |

* cited by examiner

US 11,389,592 B2

VENTING COMPONENT, CATHETER AND SYRINGE INCLUDING THE SAME

CROSS REFERENCE TO RELATED APPLICATIONS

The present application is a 35 U.S.C. 371 national stage application of a PCT International Application No. PCT/CN2019/080277, filed on Mar. 29, 2019, which claims the benefit of a Chinese Patent Application No. 201810404062.7, filed on Apr. 28, 2018, the entire disclosures of which are incorporated herein by reference.

FIELD

The present disclosure relates to the technical field of medical devices, and in particular to a venting component as well as a catheter and a syringe comprising the venting component.

BACKGROUND

During the diagnosis and treatment of some diseases, the symptoms of patients are often suppressed and improved by injecting medicines into the patients (e.g. lungs) through catheters and/or syringes.

SUMMARY

In one aspect of the present disclosure, there is provided a venting component comprising: a chamber comprising a bottom chamber and an extended chamber communicated with the bottom chamber and extending upwards therefrom, wherein the bottom chamber is configured for liquid to flow in and out, and the extended chamber comprises a support portion; a vent hole located at a side of the extended chamber away from the bottom chamber; and a floating block located in the extended chamber and forming a gap with a chamber wall of the extended chamber, wherein the floating block is configured to be supported on the support portion and is dimensioned to be able to block the vent hole.

In some exemplary embodiments, the support portion is a constricted portion formed on the chamber wall of the extended chamber that constricts towards the bottom chamber.

In some exemplary embodiments, the constricted portion has a slope shape.

In some exemplary embodiments, the floating block has a spherical shape.

In some exemplary embodiments, an aperture of the vent hole is 20%-50% of a diameter of the floating block.

In some exemplary embodiments, the venting component further comprises: a dust cap positioned at a side of the vent hole away from the bottom chamber and covering the vent hole.

In some exemplary embodiments, the chamber wall of the extended chamber extends beyond the side of the vent hole away from the bottom chamber to fix the dust cap to a portion of an inner wall of the extended chamber beyond the vent hole.

In some exemplary embodiments, the bottom chamber is configured to connect a first fluid connector and a second fluid connector to each other in an airtight sealing manner, the first fluid connector being one of a catheter and a syringe, and the second fluid connector being the other of the catheter and the syringe.

In another aspect of the present disclosure, there is provided a catheter comprising a connecting portion at a first side end and a guiding portion at a second side end thereof, wherein the catheter further comprises the venting component according to the above embodiments, wherein, the venting component is connected to the connecting portion of the catheter from the first side end; or, the venting component is fastened to and in fluid communication with the connecting portion of the catheter in an airtight sealing manner.

In still another aspect of the present disclosure, there is provided a syringe comprising a piston, a barrel and a nipple, wherein the syringe further comprises the above described venting component, wherein, the venting component is connected to the nipple; or, the venting component is fastened to and in fluid communication with the nipple of the syringe in an airtight sealing manner.

BRIEF DESCRIPTION OF THE DRAWINGS

In the drawings, which are not necessarily drawn to scale, the same reference numerals may describe similar parts in different views. The accompanying drawings generally illustrate various embodiments by way of example instead of limitation, and together with the description and claims serve to explain the disclosed embodiments. Where appropriate, the same reference numerals are used throughout the drawings to refer to the same or similar parts. Such embodiments are illustrative and are not intended to be exhaustive or exclusive embodiments of the present device or method.

DETAILED DESCRIPTION

Figure 1:
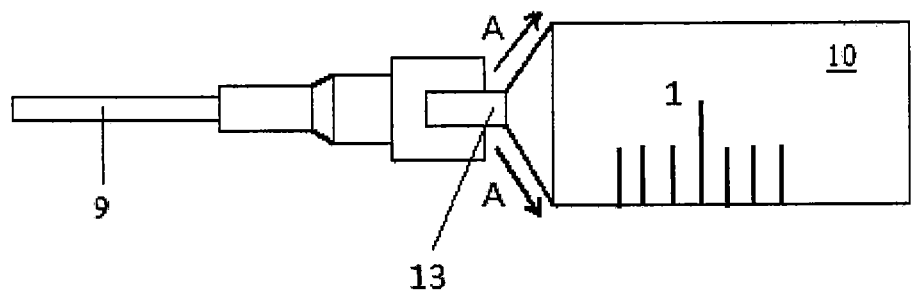
FIG. 1 shows a diagram of a situation of liquid leakage between a catheter and a syringe caused by air pressure in a body part to which the catheter is connected according to the related art.

In order to enable those skilled in the art to better understand the technical solution of the present disclosure, the present disclosure will be described in detail below with reference to the drawings and the detailed description. The embodiments of the present disclosure will be described in further detail below with reference to the drawings and specific embodiments, but not as a limitation of the present disclosure.

The following description of specific embodiments or applications is provided by way of example only. Various modifications to various embodiments will be readily apparent to those skilled in the art, and the main principles defined herein may be applied to other embodiments and applications without departing from the spirit and scope of the present disclosure. Therefore, the present disclosure is not intended to be limited to the illustrated embodiments, but is within the possible scope consistent with the principles and features disclosed therein and defined by the claims. Although each embodiment is described separately, features and elements in different embodiments may be combined with each other, and the combination mode is not limited to each independent embodiment.

The use of "first," "second," and similar words in this disclosure do not denote any order, quantity, or importance, but rather are used to distinguish different parts. Similar words such as "include" or "comprise" mean that the elements before the word cover the elements listed after the word, and do not exclude the possibility of also covering other elements. "Up", "down", "left", "right", "bottom" and "top" are only used to indicate the relative positional relationship. When the absolute position of the described object changes, the relative positional relationship may also change accordingly. As used in this disclosure, "distal" and similar words refer to a portion of a structure that is further from the user, while "proximal" and similar words refer to a portion of the structure that is closer to the user. As used in the present disclosure, the term "chamber" refers to a body having an internal cavity, and the internal cavity is formed by surrounding walls of the body.

In the present disclosure, when it is described that a specific device is located between a first device and a second device, intervening devices may or may not exist between the specific device and the first device or the second device. When it is described that a specific device is connected to other devices, the specific device may be directly connected to the other devices without intervening devices or may have intervening devices instead of being directly connected to the other devices.

All terms (including technical terms or scientific terms) used in this disclosure have the same meaning as those understood by those of ordinary skill in the art to which this disclosure belongs, unless otherwise specifically defined. It should also be understood that terms defined in, for example, a general dictionary should be interpreted as having meanings consistent with their meanings in the context of the related art, and should not be interpreted in an idealized or extremely formalized meaning, unless explicitly defined herein.

Technologies, methods and devices known to those of ordinary skill in the relevant fields may not be discussed in detail, but where appropriate, the technologies, methods and devices should be considered as part of the specification.

In the technology discovered by the inventors, when a connection structure between a catheter and a syringe as shown in FIG. 1 is used, the medicine may leak out from the fitting gap between the catheter 9 and a nipple 13 of the syringe 10 in the directions indicated by arrows A, which not only wastes the medicine, but also pollutes the treatment environment. In addition, sometimes there is a certain amount of air in the syringe or catheter, and when injecting medicines such as intramuscular or intravenous injections, injecting the air into a body together with the medicine is unfavorable to the patient's body, so the air needs to be vented in advance before injection. Based on the structure shown in FIG. 1, it is usually dependent on a manual operation of a physician to vent in advance, for example, by pushing the liquid medicine to overflow from the nipple 13 of the syringe 10 so as to expel bubbles therein, and then the nipple 13 of the syringe 10 is fitted with a needle for direct injection or connected to the catheter 9 for injection, which may cause medicine waste, especially when injecting trace expensive medicines such as insulin, and may also cause pollution to the treatment environment and bring troubles to the treatment process.

Some exemplary embodiments of the present disclosure provide a venting component as well as a catheter and a syringe including the venting component. The venting component can avoid liquid medicine backflow and liquid leakage caused by air pressure in a body part, and has a simple venting operation. Waste of liquid medicine and environmental pollution can be avoided as much as possible, thereby ensuring smooth injection. When the catheter and the syringe need to be connected for injection, the venting component can connect the catheter and the syringe to each other in an airtight sealing manner, thereby realizing the above beneficial effects on the whole flow path. The venting component can be installed or integrated in the catheter, thus avoiding liquid medicine backflow and liquid leakage caused by air pressure in the body part. It can also be installed or integrated in the syringe, thereby facilitating venting in advance before injection and reducing the waste of liquid medicine.

Figure 2:
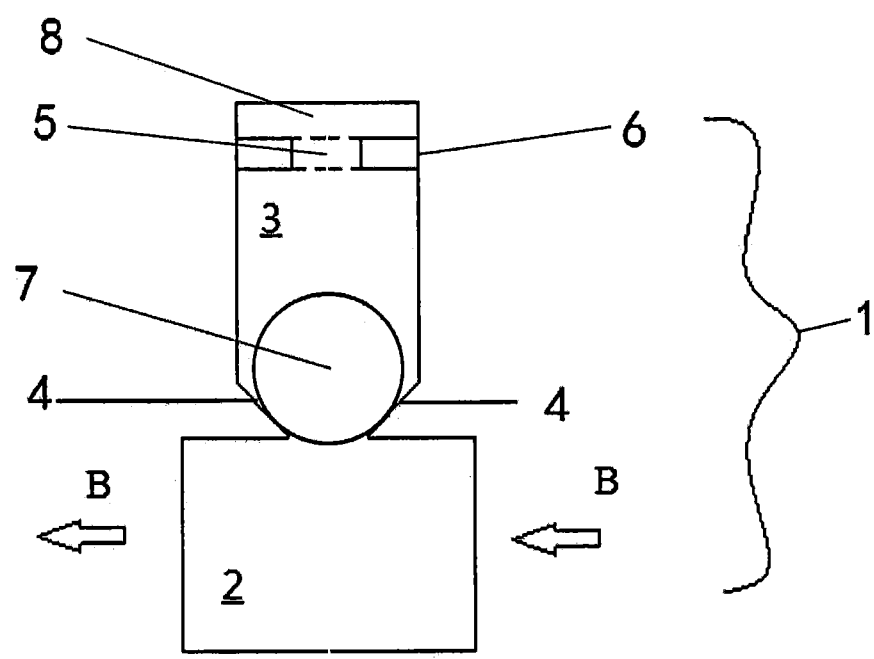
FIG. 2 shows a structural schematic view of a venting component according to some exemplary embodiments of the present disclosure.

FIG. 2 shows a structural schematic view of a venting component according to some exemplary embodiments of the present disclosure.

As shown in FIG. 2, a venting component according to some exemplary embodiments of the present disclosure includes: a chamber 1 including a bottom chamber 2 and an extended chamber 3 communicating with the bottom chamber 2 and extending upward from the bottom chamber 2. The bottom chamber 2 of the chamber 1 is configured for liquid medicine to flow in and out, e.g., in a direction indicated by arrow B or in a direction opposite to the direction indicated by arrow B. The extended chamber 3 is provided with a support portion 4; a vent hole 5 which is provided at a top 6 of the extended chamber 1; and a floating block 7 which is provided in the extended chamber 3 and forming a gap with the chamber wall of the extended chamber 3. The floating block 7 is configured to be supported on the support portion 4, and the floating block 7 is dimensioned to be able to block the vent hole 5.

Although the support portion 4 shown in FIG. 2 is located at the junction between the bottom chamber 2 and the extended chamber 3, the position of the support portion 4 and the division between the bottom chamber 2 and the extended chamber 3 are not limited to this.

The above venting components can be applied in flexible ways.

Figure 3:
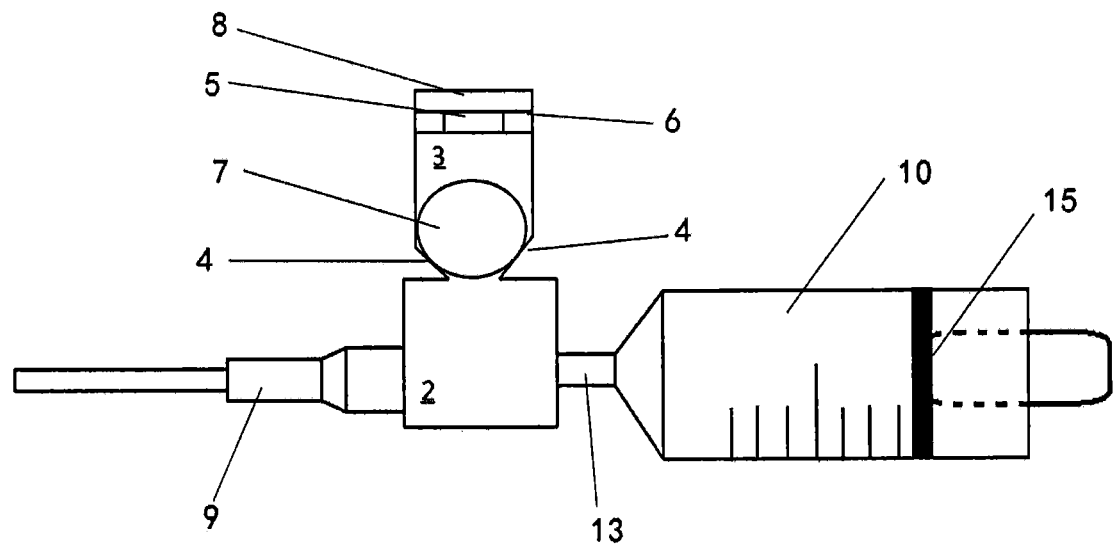
FIG. 3 shows a schematic view of a venting component that airtightly interconnects a catheter and a syringe according to some exemplary embodiments of the present disclosure.

As shown in FIG. 3, in some exemplary embodiments, one side of the bottom chamber 2 of the venting component may be airtightly connected to the catheter 9 that is connected to a patient site (e.g., lung) while the other side may be airtightly connected to the nipple 13 of the syringe 10.

The working process of the venting component will be explained by taking the application scenario where a large air pressure in the lung presses the liquid medicine toward the syringe 10 as an example. At this time, if the piston 15 of the syringe 10 is pushed to inject the liquid medicine, the venting component forms a three-way structure with the catheter 9 and the syringe 10. The air pressure in the lung and the pressure exerted by the syringe 10 act together on the air (e.g., bubbles) in the liquid medicine and push it to flow towards the top 6 of the extended chamber 3 through the gap between the floating block 7 and the chamber wall of the extended chamber 3, and then to be vented through the vent hole 5.

In some exemplary embodiments, the vent hole 5 is small to facilitate gradually venting the air, and the air transferred to the space above the floating block 7 in the extended chamber 3 but not yet vented may form an air pressure at the top space to press down the floating block 7, thus preventing it from blocking the vent hole 5 to ensure the gradual and smooth venting. Even if the floating block 7 floats up due to the disturbance of the inflow air, the air pressure formed by the temporarily trapped air at the top space can press down the floating block 7 to prevent it from blocking the vent hole 5.

In some exemplary embodiments, when the air pressure at the top space is further increased, even if the floating block 7 floats in the liquid medicine due to liquid inflow in the extended chamber 3, the air pressure may cause the liquid level in the cavity of the extended chamber 3 to drop and thus cause the floating block 7 to drop accordingly, thereby preventing the floating block 7 from blocking the vent hole 5 and ensuring the gradual and smooth venting.

In some exemplary embodiments, the density of the floating block 7 is less than that of the liquid medicine, and the weight of the floating block 7 is appropriately configured to avoid temporary blockage of the vent hole 5 caused by floating up to the vent hole 5 due to disturbance of inflow air, thereby realizing continuous venting. After the air is vented, as the liquid medicine in the chamber 1 gradually increases, when the liquid medicine in the chamber 1 reaches the bottom of the floating block 7, the floating block 7 will separate from the support portion 4 and float on the liquid medicine. As the liquid level of the liquid medicine in the chamber 1 increases, the height at which the floating block 7 is located will also increase until the floating block 7 blocks the vent hole 5. Therefore, the liquid medicine cannot be discharged from the vent hole 5, and a stable pressure is formed in the chamber 1. Also, under the coaction of the pushing force from the syringe 10, the liquid medicine is stably pressed to the distal side of the catheter 9, and the injection can be smoothly performed while avoiding liquid leakage.

Figure 4:
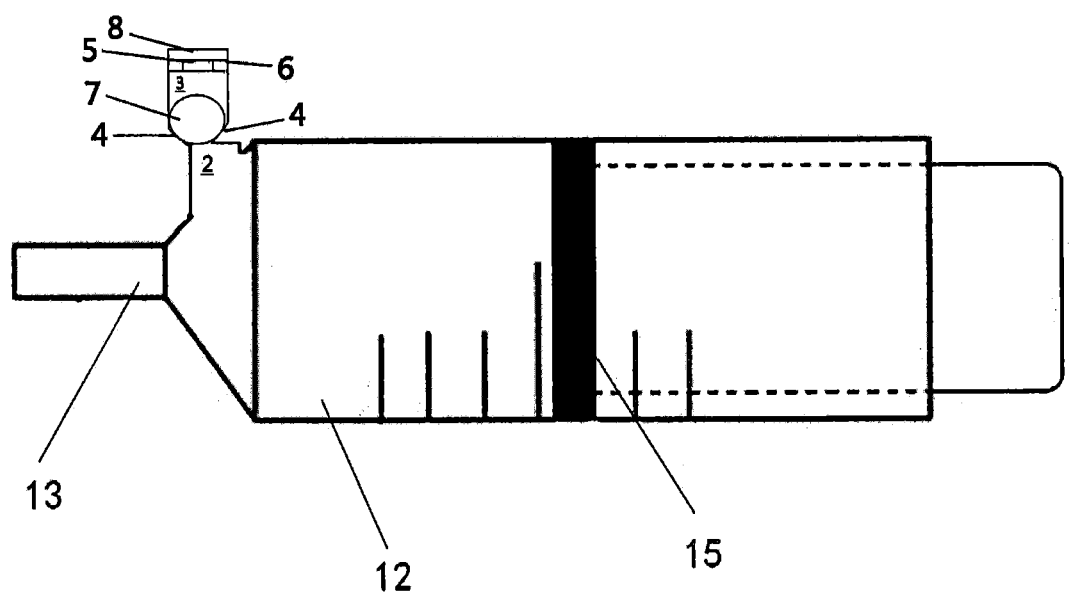
FIG. 4 shows a schematic structural view of a syringe according to some exemplary embodiments of the present disclosure.

The dimension and construction of the venting component can be adapted to suit different application scenarios. Taking the application scenario in which a syringe 10 is used to perform intravenous injection into a patient's body as an example, it is well known that it is necessary to avoid injecting air during intravenous injection, otherwise air embolism may be caused. The venting component may be integrated on the tapered wall of the nipple 13 of the syringe 10 and the inner cavity of the venting component is communicated with the inner cavity of the nipple 13. As shown in FIG. 4, the size of the venting component used in intravenous injection can be designed to be smaller than the size of the venting component used in the application scenario of the structure shown in FIG. 3. By pushing the piston 15 of the syringe 10, bubbles in the liquid medicine contained in the barrel 12 of the syringe 10 and the liquid medicine are pressed into the venting component through the outlet of the nipple 13. The liquid medicine is pushed to flow into and out of the venting component, and the bubbles in the liquid medicine float up to the space above the liquid level in the bottom chamber 2. Since the air pressure of the vein is greater than the atmospheric pressure in the chamber 1 of the venting component, when the piston 15 of the syringe 10 is pushed further, the bubbles are pushed upward and continue to float up, entering the above extended chamber 3 communicating with the bottom chamber 2, instead of entering the needle (not shown) connected to the nipple 13 and then injecting into the vein of the patient, and thus avoiding air embolism. Then, the air flows upward through the gap between the floating block 7 and the chamber wall of the extended chamber 3 and is vented through the vent hole 5, thereby realizing gradual venting of the air. After the air is gradually vented, the liquid medicine may flow into the extended chamber 3, causing the floating block 7 to float up. The continuous inflow of the liquid medicine causes the floating block 7 to rise up accordingly until the vent hole 5 is blocked. Therefore, the liquid medicine cannot be discharged from the vent hale 5, and a stable pressure is formed in the chamber 1. Also, under the coaction of the pushing force from the syringe 10, the liquid medicine after removing air is stably pressed to the vein side. The intravenous injection can be performed safely and smoothly while avoiding liquid leakage. This not only avoids the pollution of liquid leakage to the environment, but also makes the operation simpler and reduces the waste of liquid medicine compared with the prior manual venting operation of the syringe 10.

In some exemplary embodiments, the bottom chamber 2 is configured to connect a first fluid connector and a second fluid connector to each other in an airtight sealing manner, the first fluid connector being one of a catheter and a syringe, and the second fluid connector being the other of the catheter and the syringe. For example, as shown in FIG. 3, when the first fluid connector is a syringe 10 and the second fluid connector is a catheter 9, the bottom chamber 2 of the venting component forms a three-way structure with the internal cavities of the syringe 10 and the catheter 9. As mentioned above, the liquid medicine of the syringe 10 may flow into the catheter 9 through the venting component, and the air in the catheter 9 may enter the venting component and be vented through the vent hole 5 of the venting component, thus avoiding the problem that the medicine is pressed out by increased air pressure when the syringe 10 is used to inject.

In some exemplary embodiments, the first fluid connector and the second fluid connector may also be different parts of a component, for example, as described above in connection with FIG. 4, may be portions at different positions on the flow path of the tapered wall of the nipple 13 of the syringe 10, respectively.

Next, various embodiments of the venting component will be described in detail based on the structure of the venting component shown in FIG. 2.

In some exemplary embodiments, the orientations of the vent hole 5 may be up, upper left, or upper right. That is, the orientation of the vent hole 5 may be slightly inclined in the upward direction. This can prevent the liquid medicine from flowing out of the vent hole 5.

In some exemplary embodiments, the support portion 4 may be a support plate disposed and fixed in the chamber 1. In other exemplary embodiments, in order to integrally form the chamber 1, the support portion 4 may be a constricted portion formed on the chamber wall of the chamber 1 that constricts towards the bottom chamber.

In some exemplary embodiments, the constricted portion has a slope shape. The constricted portion of the slope shape is beneficial. On the one hand, when the liquid level of the liquid medicine does not reach the support portion 4, the liquid medicine accompanying the air entering the space above the floating block 7 can slide down below the floating block 7 along the slope of the constricted portion, thus improving the utilization rate of the liquid medicine. On the other hand, when the liquid level of the liquid medicine does not reach the support portion 4, the cross section of the flow path below the support portion 4 for the air below the floating block 7 is reduced, thereby improving the flow rate and facilitating the air to enter the space above the floating block 7 through the gap between the chamber wall of the slope shape and the floating block 7. Of course, the constricted portion can also be designed to have other shapes, for example, a stepped shape.

In some exemplary embodiments, the floating block 7 has a spherical shape, and the spherical floating block 7 can allow air to conveniently enter the space above the floating block 7 from the gap between the floating block 7 and the chamber wall. Even if the floating block 7 offsets and rotates in the liquid medicine due to external vibration (e.g., shaking of the physician's hand), it can still keep tightly blocking the vent hole 5.

In some exemplary embodiments, the gap between the floating block 7 and the chamber wall of the extended chamber 3 may be adjusted according to actual needs, for example in the range of 1-4 mm, to avoid liquid leakage caused by lateral offset of the floating block 7.

In some exemplary embodiments, an aperture (cross-sectional diameter) of the vent hole 5 is 20%-50% of the diameter of the spherical floating block 7. The relationship between the size of the vent hole 5 and the size of the floating block 7 enables the air pressure in the space above the floating block 7 to accumulate and not to be rapidly vented through the vent hole 5, thus ensuring that the floating block 7 does not rise to the vent hole 5 to directly block the vent hole 5.

In some exemplary embodiments, the venting component further comprises a dust cap 8 positioned at the top 6 of the chamber 1 and covering at least the vent hole 5. Since the vent hole 5 is located below the dust cap 8, the arrangement of the dust cap 8 can prevent dust and bacteria in the environment from entering the interior of the venting component to pollute the venting component, and the venting component can be used several times.

In some exemplary embodiments, the chamber wall of the extended chamber 3 extends above the vent hole 5 to fasten the dust cap 8 to a portion of the inner wall of the chamber 1 above the vent hole 5. Fastening the dust cap 8 to the inner wall of the chamber 1, for example, adhering the periphery of the dust cap 8 to the inner wall of the chamber 1, can prevent human hands from touching the dust cap 8.

The venting component described above can not only interconnect the catheter 9 and the nipple 13 of the syringe 10, but also be incorporated (e.g., fastened or integrated) in the catheter 9 or the syringe 10 to form the catheter 9 or the syringe 10 with a built-in venting function.

Figure 5:
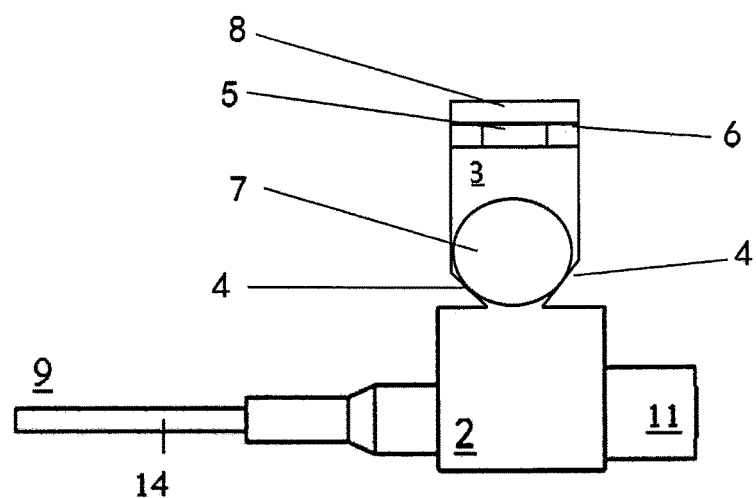
FIG. 5 shows a schematic structural view of a catheter according to some exemplary embodiments of the present disclosure.

FIG. 5 shows a schematic structural view of a catheter 9 according to some exemplary embodiments of the present disclosure. As shown in FIG. 5, the catheter 9 comprises a connecting portion 11 at a first end (a proximal end with respect to the distance of the venting component) and a guiding portion 14 at a second end (a distal end with respect to the distance of the venting component). The guiding portion 14 is used to deliver the liquid medicine into a patient's body. The catheter 9 further includes the venting component described above. The venting component is fastened to and in fluid communication with the connecting portion 11 of the catheter in an airtight sealing manner, so that the syringe 10 or other liquid medicine source is connected to the connecting portion 11 of the catheter 9 to inject the liquid medicine into the guiding portion 14 of the catheter 9 through the venting component.

In some exemplary embodiments, the venting component may be connected from the proximal end to the connecting portion 11 of the catheter, so that the syringe 10 or other liquid medicine source may be connected to a proximal port of the bottom chamber 2 of the venting component to inject liquid medicine into the catheter 9 through the venting component. The venting process of the venting component is similar to that of the above-described embodiment and will not be repeated here.

As shown in FIG. 4, some exemplary embodiments of the present disclosure also provide a syringe 10, which comprises a piston 15, a barrel 12, a nipple 13, and the above-described venting component. The venting component is fastened to and in fluid communication with the nipple 13 of the syringe 10 in an airtight sealing manner, so that the liquid medicine in the syringe 10 can be injected into a patient's body from a port of the nipple 13 via the venting component.

In some exemplary embodiments, a fluid connector such as a catheter 9 may be airtightly connected to the port of the nipple 13, so that the liquid medicine in the syringe 10 may be transferred from the port of the nipple 13 into the connected fluid connector via the venting component on the nipple 13 (e.g., on the sidewall) and injected into a patient's body from the fluid connector.

In some exemplary embodiments, the venting component may also be connected to the nipple 13, and the catheter 9 or other fluid connectors may be connected to the venting component to transfer the liquid medicine in the syringe 10 to the catheter 9 or other fluid connectors through the venting component and inject it into a patient's body from the catheter 9 or other fluid connectors. The specific venting process of the venting component is similar to the application scenario described above with reference to FIGS. 2-4, and will not be repeated here.

The venting component as well as the catheter and the syringe comprising the venting component provided by the present disclosure have the beneficial effects that after individual injection members such as the catheter and/or the syringe are assembled, air can be vented from the vent hole of the venting component automatically in the injection process by directly using the venting component disclosed by the disclosure, an airtight seal with respect to the outside is automatically generated after the air is vented so that the liquid medicine can smoothly enter the patient's body through the bottom chamber of the venting component without being pressed out by air pressure or leaking into the outside environment, the physician has simple operation, and the smooth injection process can be ensured.

The above embodiments are merely exemplary embodiments of the present disclosure and are not intended to limit the present disclosure. The scope of protection of the present disclosure is defined by the claims. Those skilled in the art can make various modifications or equivalent substitutions to the disclosure within the spirit and scope of protection of the disclosure, and such modifications or equivalent substitutions should also be regarded as falling within the scope of protection of the disclosure.

The invention claimed is:
1. A venting component comprising:
   a chamber comprising a bottom chamber and an extended chamber configured to communicate with the bottom chamber and extending upwards therefrom, wherein the bottom chamber is configured for liquid to flow in and out, and the extended chamber comprises a support portion;
   a vent hole at a side of the extended chamber away from the bottom chamber;
   a floating block in the extended chamber and forming a gap with a chamber wall of the extended chamber, wherein the floating block is configured to be supported on the support portion and is dimensioned to be able to block the vent hole; and a dust cap positioned at a side of the vent hole away from the bottom chamber and covering the vent hole, wherein the chamber wall of the extended chamber extends beyond the side of the vent hole away from the bottom chamber to fix the dust cap to a portion of an inner wall of the extended chamber beyond the vent hole.

2. The venting component according to claim 1, wherein the support portion is a constricted portion formed on the chamber wall of the extended chamber that constricts towards the bottom chamber.

3. The venting component according to claim 2, wherein the constricted portion has a slope shape.

4. The venting component according to claim 1, wherein the floating block has a spherical shape.

5. The venting component according to claim 4, wherein an aperture of the vent hole is 20%-50% of a diameter of the floating block.

6. The venting component according to claim 1, wherein the bottom chamber is configured to connect a first fluid connector and a second fluid connector to each other in an airtight sealing manner, the first fluid connector comprises one of a catheter and a syringe, and the second fluid connector another of the catheter and the syringe.

7. A catheter comprising:
a connecting portion at a first side end thereof and a guiding portion at a second side end thereof, and
the venting component according to claim 1,
wherein the venting component is configured into one of the following:
the venting component is connected to the connecting portion of the catheter from the first side end; or
the venting component is fastened to and in fluid communication with the connecting portion of the catheter in an airtight sealing manner.

8. A syringe comprising a piston, a barrel, a nipple and the venting component according to claim 1,
wherein the venting component is configured into one of the following:
the venting component is connected to the nipple; or
the venting component is fastened to and in fluid communication with the nipple of the syringe in an airtight sealing manner.

9. The syringe according to claim 8, wherein the support portion is a constricted portion formed on the chamber wall of the extended chamber that constricts towards the bottom chamber.

10. The syringe according to claim 9, wherein the constricted portion has a slope shape.

11. The syringe according to claim 8, wherein the floating block has a spherical shape.

12. The syringe according to claim 11, wherein an aperture of the vent hole is 20%-50% of a diameter of the floating block.

13. The syringe according to claim 8,
wherein the bottom chamber is configured to connect a first fluid connector and a second fluid connector to each other with an airtight sealing,
wherein the first fluid connector comprises one of a catheter and the syringe, and
wherein the second fluid connector comprises another of the catheter and the syringe.

* * * * *